United States Patent [19]

Kim

[11] 4,263,343
[45] Apr. 21, 1981

[54] REFERENCE ELEMENTS FOR ION-SELECTIVE MEMBRANE ELECTRODES

[75] Inventor: Sang H. Kim, Rochester, N.Y.

[73] Assignee: Eastman Kodak Company, Rochester, N.Y.

[21] Appl. No.: 66,124

[22] Filed: Aug. 13, 1979

[51] Int. Cl.³ .................. B05D 5/12; G01N 27/26
[52] U.S. Cl. .................. 427/125; 427/126.1; 427/333; 204/195 F; 204/195 M; 204/195 P; 148/6.14 R
[58] Field of Search .............. 427/126, 333, 126.1, 427/125; 204/195 R, 195 H, 195 M, 195 P; 148/6.14 R

[56] References Cited

U.S. PATENT DOCUMENTS

| | | | |
|---|---|---|---|
| 3,562,129 | 8/1967 | Simon | 204/195 M |
| 3,753,887 | 8/1973 | Kedem et al. | 204/195 M |
| 3,856,649 | 12/1974 | Genshaw et al. | 204/195 F |

FOREIGN PATENT DOCUMENTS 1375446 11/1974 United Kingdom .

OTHER PUBLICATIONS

*Research Disclosure* 16113, vol. 161, Sep. 1977, pp. 29-39.

*Primary Examiner*—Ralph S. Kendall
*Assistant Examiner*—Richard Bueker
*Attorney, Agent, or Firm*—Arthur H. Rosenstein

[57] ABSTRACT

A reference element for ion-selective membrane electrodes is prepared by coating portions of a layer of silver with a composition comprising a metal salt electrolyte, a hydrophilic binder and a membrane of the group consisting of an oxidizing agent and a silver halide emulsion.

6 Claims, 1 Drawing Figure

REFERENCE ELEMENTS FOR ION-SELECTIVE MEMBRANE ELECTRODES

This application relates to a process for preparing a reference element for ion-selective membrane electrodes and ion-selective membrane electrodes containing these elements.

The use of electrodes for the measurement of various ionic solutions is widespread. Typically, devices for obtaining such measurements include a reference electrode and a separate ion-selective electrode. When simultaneously contacted with the body of solution to be analyzed, the reference and ion-selective electrodes constitute an electrochemical cell, across which a potential develops. Measurement of the potential determines the concentration of ions in the solution.

One useful reference element for ion-selective electrodes comprises a metal in contact with an insoluble salt of the metal which is in turn in contact with an electrolyte, i.e., a solution containing the anion of the salt. A very commonly used example of such a reference element can be represented as Ag/AgCl/"X$\underline{M}$Cl$^-$" (XMCl$^-$ indicating a solution of known Cl$^-$ concentration) and comprises a silver wire having a coating of silver chloride applied thereto by dipping into an aqueous solution of known chloride concentration.

The silver halide layer of the reference electrode is conventionally coated on the silver substrate by contacting the silver substrate with an oxidizing agent and drying prior to overcoating with an electrolyte layer.

In copending U.S. application Ser. No. 893,656 of Battaglia et al, filed Apr. 5, 1978 and now U.S. Pat. No. 4,214,968, a reference element is described which is formed by coating a support such as poly(ethylene terephthalate) with a metallic silver layer, such as by plating techniques, and treating the silver layer overall with an oxidizing agent or a silver halide emulsion and drying. The surface of the silver layer is thus converted to or coated by silver halide. The layer is dried and the silver halide layer is overcoated with an electrolyte layer comprising the metal salt forming the electrolyte and a hydrophilic binder. The resulting reference element is a substrate overall coated with a silver layer, overall coated with a silver halide layer and overall coated with the electrolyte layer. A membrane layer is added and the resulting ion-selective electrode is completed by connecting a probe through the various layers to the silver layer for contact.

Although the above method results in an acceptable reference element, the method is costly, as it involves a plurality of steps, and the electrical contact of the probe with the silver layer is not always good, as the probe must be forced through the membrane, electrolyte and silver halide layers to make contact with the silver layer.

SUMMARY OF THE INVENTION

According to the present invention, there is provided a novel method for preparing a metal/silver halide reference element comprising coating portions of a metal layer with a metal salt electrolyte, a hydrophilic binder and a member of the group consisting of an oxidizing agent and a silver halide emulsion.

This process is relatively inexpensive, as it requires only one step in coating the metal layer to achieve the metal layer having coated thereover a silver halide layer and an electrolyte layer, and the resulting electrode contains uncoated portions of silver which can be easily contacted with a probe.

According to a further embodiment of the present invention, an ion-selective electrode is prepared by overall coating a support with a metal, coating portions of the metal with a composition comprising a metal salt electrolyte, a hydrophilic binder and a member selected from the group consisting of an oxidizing agent and a silver halide emulsion and overcoating with a hydrophobic membrane layer containing an ionophore and an ion-carrier solvent and a hydrophobic binder. The membrane layer is useful in electrodes which measure ions, such as potassium, carbonate and the like.

In a further embodiment of this invention, a metal/silver halide reference element comprises a support containing a layer of metal, portions of said layer of metal having thereon a composition comprising a metal salt electrolyte, a hydrophilic binder and a member of the group consisting of an oxidizing agent and a silver halide emulsion; portions of said layer of metal being free from said composition.

DESCRIPTION OF THE DRAWING

The FIGURE shows a cross-sectional view of an ion-selective element as described herein.

DESCRIPTION OF THE PREFERRED EMBODIMENTS

Figure 1:
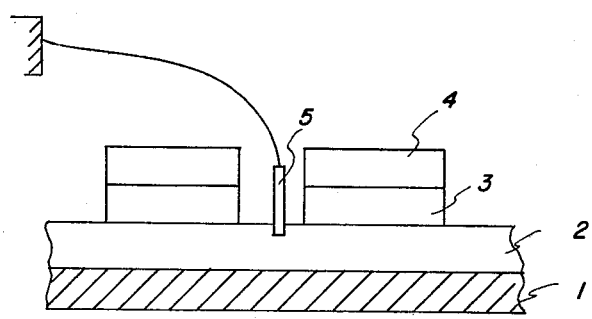

The reference elements of the present invention are prepared by coating portions of a metal layer with a composition comprising a metal salt electrolyte, a hydrophilic binder and a member of the group consisting of an oxidizing agent and a silver halide emulsion.

The metal layer need only comprise a conductive metal such as silver, nickel, copper and the like. The preferred metal is silver. The metal layer can either be self-supported or coated on a support. Suitable supports for a silver layer are preferably insulating and include glass, paper and polymeric supports, such as polyesters such as poly(ethylene terephthalate), cellulose ester materials and the like.

The metal layer can be formed in situ or coated onto a support using any suitable method of depositing the metal. In the case of silver, the silver layer, preferably a thin layer, can be formed by electroless deposition, vacuum-depositing silver, depositing a photographic silver halide layer and exposing and developing to form silver, and the like.

Portions of the metal layer are then coated with the composition containing the metal salt electrolyte, oxidizing agent or silver halide emulsion and hydrophilic binder. The coating supplies not only the silver halide layer, but also the electrolyte layer of the reference element.

The composition can be coated onto the metal using any conventional coating technique. The coating is applied, however, to only a portion of the metal layer, leaving the remainder of the layer uncoated. In a preferred embodiment, the composition is applied in stripes to the metal layer by roll coating, dipping, laminating, brush coating or other coating techniques. After application, the coating is dried, preferably at ~20° C. to ~95° C. for 1 to 30 minutes. The resulting reference element comprises the support coated with a metal layer which is then stripe-coated with a silver halide layer coated with the electrolyte layer.

By "coating portions of a metal layer" it is meant that the metal layer would, in some areas, be coated and in other areas be uncoated. The most preferable method of partially coating the metal layer is to coat in a striped fashion. That is, the coating is applied in individual striped areas leaving the remainder of the metal layer uncoated. Likewise, when a membrane layer, and optionally an overcoat layer, is applied, it is applied in the same areas as the reference coating, so that the same portions of the metal layer remain uncoated.

The coating composition comprises a metal salt electrolyte in solid solution with a hydrophilic binder. In a preferred embodiment, the portion of the cation of said salt comprises the ion which the electrode is designed to detect. Typically, the binder and salt are in solution with a solvent for both.

The binder for the electrolyte solution may comprise any hydrophilic material suitable for the formation of continuous, coherent, cohesive layers compatible with the salt of the electrolyte layer and, if formed by coating, a solvent for both the ionic salt and the polymeric binder. Preferred materials of this type are hydrophilic, natural and synthetic polymeric film-forming materials, such as polyvinyl alcohol, gelatin, agarose, deionized gelatin, polyacrylamide, polyvinyl pyrrolidone, hydroxyethyl acrylate, hydroxyethyl methacrylate, polyacrylic acid, etc. Specifically preferred from among these materials are the hydrophilic colloids, such as gelatin (especially deionized gelatin), agarose, polyvinyl alcohol and hydroxyethyl acrylate.

The ionic salt which is dissolved in the polymeric binder solution will be determined by the composition of the Ag/Ag halide layer to be formed. For example, in a potassium-selective electrode which uses AgCl as the insoluble metal salt, potassium chloride is a logical choice, although sodium chloride, etc, may also be used. For sodium ion determinations in a similar configuration, sodium chloride would be useful, etc. Thus, the salt will generally be a water-soluble salt having a cation selected from ammonium, alkali metals and alkaline earth metals, mixtures of the same or any other suitable cation to which the electrode responds, and as anion a halogen or sulfur, depending upon the composition of the metal-salt layer. Conductive metal salts of these anions are commonly insoluble.

The composition also comprises a member selected from the group consisting of an oxidizing agent and a silver halide emulsion. The oxidizing agent can be any material whose electrode potentials are more positive than standard electrode potentials of the metal being coated ($Ag^+ + e = Ag$, 0.7996V).

Examples of useful oxidizing agents are $KClCrO_3$, $K_3Fe(CN)_6$, $KMnO_4$, $K_2Cr_2O_7$, $NH_4VO_3$, $(NH_4)_2Ce(NO_3)_6$, $Fe(C_2O_4)_3$ and the like. Preferred oxidizing agents are $KClCrO_3$ and $K_3Fe(CN)_6$. Combinations of oxidizing agents can be used. A more thorough listing of oxidizing agents useful herein can be found in *Handbook of Chemistry and Physics*, 50th Edition, The Chemical Rubber Company, 1969, pp D109–114.

The amount of oxidizing agent used can vary depending on its oxidizing power, but preferably the coverage should be between 0.01 and 1.0 $g/m^2$. If an oxidizing agent is used, the metal conducting layer should be silver.

The composition can alternatively comprise a silver halide emulsion to effect the silver halide layer. In such case, the silver halide is in the form of an emulsion with the hydrophilic binder in the coating composition and the metal conducting layer can be other than silver. The silver halide can comprise silver chloride, silver bromide, silver iodide, silver bromoiodide and the like. Varying coverages of silver halide and a hydrophilic binder such as gelatin can be used, but preferably the coverage of silver halide is from 1.16 to 1.83 $g/m^2$ of silver as silver halide in 0.054 to 0.54 $g/m^2$ gelatin.

The composition to be coated over the metal layer can generally comprise from about 0.1 to about 7.5 $g/m^2$ of metal salt electrolyte and from about 0.5 to about 10 $g/m^2$ of hydrophilic binder. Generally, salt concentrations of from about 30% to about 50% by weight binders in the layer are preferred.

The coating compositions can also contain other addenda, such as surfactants, for example saponin, Surfactant 10G and the like; buffering agents, such as NaOH, HCl, phosphate, acetic acid and the like.

Appropriate solvents for the polymeric binder and ionic salt will depend largely on the nature of the polymer and the salt. Generally, polar solvents suitable for dissolving the salt and the polymer are satisfactory. Thus, water is a preferred solvent for layers of hydrophilic materials, such as polyvinyl alcohol and gelatin.

The coating composition can be formulated by merely adding the metal salt electrolyte and oxidizing agent or silver halide emulsion to a hydrophilic binder, such as gelatin, in the presence of water and drying.

Since the thickness of the "dried" electrolyte layer will, to some extent, determine the response characteristics of the electrode, it is generally desirable to maintain the "dried" layer rather thin. Layers having dry thicknesses on the order of from about 0.1 to about 0.5 mil have been found useful. A preferred thickness is about 0.2 mil. Of course, where electrode response characteristics are not critical, the thickness of the layer may vary over a wide range. The application of sound engineering skills and the use requirements of the finished electrode will determine its limits.

The reference elements described above are particularly useful in dry operative ion-selective electrodes, which require a membrane layer containing an ionophore.

The electrodes generally can comprise the reference element described above in a conventional solution electrode such as a barrel electrode or can be in the form of a dry operative electrode (both as described in *Research Disclosure* 16113, published by Industrial Opportunities Limited, Homewell, Havant, Hampshire, PO9, 1EF, UK, Volume 161, September, 1977). Solution assays can be carried out, for example, in barrel type electrodes containing electrode bodies having therein a membrane. The sample is contacted to the membrane and a reference electrode is inserted into the electrode body.

Dry operative electrodes are those described in U.S. application Ser. No. 893,656 and comprise a reference electrode layer coated with an electrolyte layer and a membrane layer.

The membrane of the electrode designed to measure potassium, sodium, $CO_2$, and other ions requiring a membrane can be coated over the reference element by any means, such as roll coating, dip coating and the like.

The ion-selective membrane can be any membrane layer known in the art.

Among the patents and publications which describe ion-selective membranes of the type useful in the instant invention, the contents of which are incorporated herein by reference to the extent that they are pertinent, are:

U.S. Pat. No. 3,562,129 to Simon, issued Feb. 9, 1971;
U.S. Pat. No. 3,753,887 to Kedem et al, issued Aug. 21, 1973;
U.S. Pat. No. 3,856,649 to Genshaw et al, issued Dec. 24, 1974;
British Pat. No. 1,375,446, issued Nov. 27, 1974;
German OLS No. 2,251,287, issued Apr. 26, 1973;
W. E. Morf, G. Kohr and W. Simon, "Reduction of the Anion Interference in Neutral Carrier Liquid-Membrane Electrodes Responsive to Cations", *Analytical Letters*, Volume 7, No. 1, pages 9 through 22 (1974);
W. E. Morf, D. Ammann, E. Pretsch and W. Simon, "Carrier Antibiotics and Model Compounds as Components of Ion-Sensitive Electrodes", *Pure and Applied Chemistry*, Volume 36, No. 4, pages 421 through 439 (1973);
D. Ammann, E. Pretsch and W. Simon, "Sodium Ion-Selective Electrode Based on a Neutral Carrier", *Analytical Letters*, Volume 7, No. 1, pages 23 through 32 (1974);
R. W. Cattrall and H. Freiser, *Analytical Chemistry*, 43, 1905 (1971); and
H. James, G. Carmack and H. Freiser, *Analytical Chemistry*, 44, 856 (1972).

Membranes of this type are well known. Such membranes generally include an inert hydrophobic binder or matrix having dispersed therein an ion carrier or selector commonly referred to as an ionophore which imparts selectivity to the membrane. These membranes can also contain a carrier solvent for the ionophore to provide adequate ion mobility in the membrane. The carrier solvent generally also serves as a plasticizer for the membrane binder.

The membrane layer generally contains binders, ion carriers, solvents and the like, such as described in co-pending U.S. application Ser. No. 893,656, filed Apr. 5, 1978.

The ion-selective electrodes can be manufactured using a conductive wire as the starting material and dipping the wire sequentially into the reference composition and the composition containing the membrane; or a dry operative electrode can be prepared by coating, laminating or otherwise applying the individual layers one over another to form a planar, multilayer electrode structure.

Thus, as seen in FIG. 1, a typical manufacturing procedure for a metal-insoluble metal salt-electrolyte reference element would involve applying the reference composition 3 to a layer of silver 2 vacuum-deposited on a poly(ethylene terephthalate) support 1, drying, overcoating the reference element with a solution 4 of the components of the ion-selective membrane and drying to provide a complete electrode. Alternatively, the layers can be laminated, so long as intimate contact between layers is achieved and maintained, and uniformity of thickness of the ion-selective membrane is attained. A potential is set up using the probe 5 connected to the silver layer.

The particular drying conditions which must be applied to the reference element in the manufacture of any specific ion-selective electrode will, of course, vary greatly, depending upon the composition of the electrode layers, particularly the binder used, the solvent or dispersing medium used to form the layer, and these can be readily determined by the skilled artisan. Typical such conditions are described in the examples below for layers of the composition described therein.

The ion selectively of membrane electrodes can be observed by measuring a steady-state difference in electrical potential between reference solutions and sample solutions, as described in the above-identified U.S. application Ser. No. 893,656.

The following examples will serve to better demonstrate the successful practice of the present invention.

EXAMPLE 1

A silver-coated poly(ethylene terephthalate) support was stripe-coated with an electrolyte layer containing, in 5 g/m$^2$ of gelatin, chloride salts and oxidizing agents, as shown in Table I. A carbonate-sensitive membrane containing 6 g/m$^2$ poly(vinyl chloride) (VYNS® (Union Carbide)), 4 g/m$^2$ poly(vinyl acetate) VAGH® (Union Carbide), 5 g/m$^2$ 4-decyltrifluoroacetophenone, 10 g/m$^2$ diisodecylphthalate, 1.25 g/m$^2$ trioctylpropylammonium chloride and 0.05 g/m$^2$ surfactant containing a mixture of polydimethylphenyl siloxane and polymethylphenyl siloxane (Dow Corning 510 fluid) was coated over the reference elements in the areas coated with the electrolyte layer. A control reference element was prepared according to the methods of the prior art by overall coating the silver-coated support with an oxidizing agent to form a silver layer. The reference electrode was then subsequently overcoated in striped fashion with an electrolyte layer containing gelatin and chloride salts. The membrane layer was stripe coated over the electrolyte layer. The electrodes were tested in the absolute mode using an Ag/AgCl reference electrode and saline samples containing 10, 40 and 100 mM HCO$_3^-$ buffered with tris-HCl (pH 8.25, 0.062–0.576 mM carbonate activities).

The results shown in Table I indicate that the electrodes prepared by the method of the present invention exhibit stable potential-time profiles that are comparable to the control. The figure Sy.x indicated how well the data points fit on a straight line when plotted. Low Sy.x figures indicate the reproducibility of the data is excellent.

TABLE I

| Example | 5 g/m$^2$ Gelatin Reference Layer[1] | | | | | | |
|---|---|---|---|---|---|---|---|
| | | | Oxidizing Agents | | | Slope ± SD | Sy . X |
| (Electrode) | NaCl | KCl | KClCrO$_3$ | K$_3$Fe(CN)$_6$ | Base | mv/dec | mV |
| Control 1 | 1.88 | 0.63 | — | — | AgCl | −24.9 ± 1.3 | 1.69 |
| Control 2 | 1.88 | 0.63 | — | — | Ag | −35.4 ± 5.7 | 7.84 |
| 1A | 2.4 | — | 0.1 | — | Ag | −28.4 ± 1.6 | 2.19 |
| 1B | 2.1 | — | 0.4 | — | Ag | −19.6 ± 1.5 | 2.05 |
| 1C | 2.4 | — | — | 0.1 | Ag | −34.1 ± 2.0 | 2.80 |
| 1D | 2.1 | — | — | 0.4 | Ag | −28.2 ± 1.8 | 2.47 |
| | | | | | Ideal Value = −29.0 | | |

[1]All units in g/m$^2$

EXAMPLE 2

Reference elements prepared as shown in Table II were overcoated with carbonate-sensitive membranes as in Example 1.

TABLE II

| Example | NaCl | KClCrO$_3$ | K$_3$Fe(CN)$_6$ | Base |
| --- | --- | --- | --- | --- |
| Control | — | — | — | AgCl |
| 2A | 2.4 | 0.1 | — | Ag |
| 2B | 2.1 | — | 0.4 | Ag |

The electrodes were tested in a differential mode using a buffered CO$_2$ calibrator containing 30.22 mM CO$_2$ as the reference solution and one containing 59.67 mM CO$_2$ as the sample solution. The results shown in Table III indicate that incorporated oxidizing agents surprisingly do not adversely affect the electrode behavior, i.e., the potentials obtained from the electrodes coated by the method of the present invention are similar to those of the control electrode. This is unexpected, as the electrodes are generally sensitive to interference and one would expect the addition of oxidizing agents to interfere. Consistently good contact was made to the silver layer in the examples (as evidenced by the low rate of rejections of Example 2B).

TABLE III

| Example | Potential | SD | Total Number of Runs | Percent Rejected |
| --- | --- | --- | --- | --- |
| Control | −5.1 mV | 0.8 mV | 23 | 4 |
| 2A | −5.8 mV | 2.0 mV | 22 | 8 |
| 2B | −4.7 mV | 0.9 mV | 24 | 0 |

EXAMPLE 3

A silver-coated polyethylene terephthalate support was coated in striped fashion with an electrolyte layer containing in 5 g/m$^2$ of gel: a photographic-type, silver-chloride emulsion (10 g/m$^2$), KNO$_3$ (0.83 g/m$^2$) (optional) and octylphenoxy polyethoxyethanol (Triton ® X-100, Rohm and Haas Company) (0.2 g/m$^2$). A control reference element was prepared according to the method of the control element of Example 1. The reference elements were overcoated with carbonate-sensitive membrane layers as above and evaluated using absolute measurements against a Ag/AgCl reference electrode. Tris-HCl buffered calibrator solutions containing 1, 4, 10, 40 and 100 mM concentrations of HCO$_3^-$ were used in testing the electrodes (pH 8.25, 0.006–0.576 mM carbonate activities). As can be seen in Table IV, the emulsion-containing electrode responded similarly to the control electrode. Therefore, this method of the present invention simplified manufacture of the reference element with adequate performance and provided good contact through the uncoated silver layer.

TABLE IV

| Example | Slope | Standard Error of Slope | $S_{y.x}$* |
| --- | --- | --- | --- |
| Control | −25.9 mV/dec | 0.61 | 1.5 |
| 3 | −24.5 mV/dec | 0.70 | 1.7 |

*All measurements in mV.

The invention has been described in detail with particular reference to preferred embodiments thereof, but it will be understood that variations and modifications can be effected within the spirit and scope of the invention.

I claim:

1. A process of preparing a metal/silver halide reference element comprising coating portions of a metal support, or a metal layer on a support, with a composition comprising a metal salt electrolyte having a cation which is selected from ammonium, alkali metals and alkaline earth metals and an anion which is a halogen or sulfur, a hydrophilic binder and a member of the group consisting of an oxidizing agent and a silver halide emulsion, with the proviso that if the oxidizing agent is used, the metal layer or metal support is silver and at least one of the metal salt electrolyte and oxidizing agent contains halide ions.

2. The process of claim 1 wherein the coating contains a silver oxidizing agent and the metal is silver.

3. The process of claim 2 wherein the silver oxidizing agent is selected from the group consisting of KClCrO$_3$, K$_3$Fe(CN)$_6$, KMnO$_4$, K$_2$Cr$_2$O$_7$, NH$_4$VO$_3$, (NH$_4$)$_2$Ce(NO$_3$)$_6$ and Fe$_2$(C$_2$O$_4$)$_3$.

4. The process of claim 1 wherein the metal layer is coated on a support.

5. The process of claim 1 wherein the coating contains a silver halide emulsion.

6. The process of claim 1 wherein the metal salt electrolyte is selected from the group consisting of halides of ammonium, alkali and alkaline earth.

* * * * *